United States Patent [19]

Mochizuki et al.

[11] Patent Number: 4,804,450
[45] Date of Patent: Feb. 14, 1989

[54] APPARATUS FOR FUSING CELLS

[75] Inventors: Takanori Mochizuki; Kenzo Toda, both of Kyoto; Mamoru Koga, Otsu; Yoshiyuki Togawa, Osaka; Shinitiro Takayama, Kyoto; Katsuyuki Imai, Otsu, all of Japan

[73] Assignee: Shimadzu Corporation, Kyoto, Japan

[21] Appl. No.: 940,119

[22] Filed: Dec. 10, 1986

[30] Foreign Application Priority Data

Dec. 11, 1985 [JP] Japan ............... 60-191185[U]
Dec. 13, 1985 [JP] Japan ............... 60-191936
Dec. 13, 1985 [JP] Japan ............... 60-280566

[51] Int. Cl.[4] ............... C12N 15/00; C12N 13/00
[52] U.S. Cl. ............... 204/299 R; 204/180.1; 435/172.2; 435/173; 435/287; 935/93
[58] Field of Search ...... 204/299 R, DIG. 8, DIG. 9, 204/180.1; 435/172.2, 173, 89–95, 287

[56] References Cited

U.S. PATENT DOCUMENTS

| 4,441,972 | 4/1984 | Pohl | 204/183.1 |
| 4,561,961 | 12/1985 | Hofmann | 935/93 X |
| 4,578,167 | 3/1986 | Schoner | 204/299 R |
| 4,578,168 | 3/1986 | Hofmann | |

FOREIGN PATENT DOCUMENTS

| 0133978 | 5/1985 | European Pat. Off. | 435/173 |
| 213360 | 9/1984 | Fed. Rep. of Germany | |
| 3321239 | 12/1984 | Fed. Rep. of Germany | 935/93 |
| 3501865 | 7/1986 | Fed. Rep. of Germany | 435/173 |
| 61-11168 | 5/1986 | Japan | 435/173 |

OTHER PUBLICATIONS

J. W. Watts and J. M. King, "A Simple Method for Large Scale Electrofusion and Culture Of Plant Protoplasts", Bioscience Reports 4 (1984), pp. 335–342.
K. Kinosita, Jr. and T. Y. Tsong, "Hemolysis Of Human Erythrocytes by a Transient Electric Field", Proc. Natl. Acad. Sci. USA., vol. 74, No. 5, pp. 1923–1927, May 1977.
U. Zimmermann and J. Vienken, "Electric Field Induced Cell to Cell Fusion", J. Membrane Biol. 67, 165–182 (1982).

Primary Examiner—John F. Niebling
Assistant Examiner—John S. Starsiak, Jr.
Attorney, Agent, or Firm—Fidelman & Wolffe

[57] ABSTRACT

Apparatus for fusing cells, wherein the fusion chamber is provided with a pair of spaced electrodes whose opposite surfaces have such a vertical dimension as to prevent any nonuniform electric field from adversely affecting fusion of cells. The electrodes may comprise a pair of parallel plate electrodes or cocentrically arranged hollow cylindrical electrodes the outer one of which has an inner circumferential surface of a first radius while the inner electrode has an outer circumferential surface of a second radius smaller than the first radius, the difference between the first and second radii being sufficiently small as compared with the whole length of the radii.

13 Claims, 4 Drawing Sheets

APPARATUS FOR FUSING CELLS

BACKGROUND OF THE INVENTION

This invention relates to an apparatus for fusing cells by applying an electrical stimulus to them.

Generally, the apparatus comprises a chamber enclosing a pair of spaced electrodes between which a suspension containing cells of two different species to be fused together are put, a source of electrical stimulus, means for applying an electrical stimulus to the cells through the electrodes, and a controller for controlling the application of the electrical stimulus to the cells.

As the electrical stimulus an alternating current (AC) field and a direct current (DC) pulse are used, and as the electrodes a pair of wire or plate electrodes are used.

For effecting cell fusion an AC field is first applied through the electrodes to the cells suspended in a solution put between the electrodes to cause close membrane contact between adjacent cells, and then a DC pulse of a relatively high electric field is applied to the cells to fuse them together.

If a pair of wire electrodes are used, the following problems are encountered:

(1) The strength of the electric field between the electrodes is not uniform, so that it is difficult to accurately know the effective strength of the electric field applied to the cells.

(2) The fused cells adhere to the electrodes, so that when they are separated from the electrodes, they are damaged or broken.

(3) Multi-fusion occurs, that is, three or more cells are linked like a pearl chain.

There is also known an apparatus which uses a pair of parallel plate electrodes to which a DC voltage is applied for fusing the cells that fill the space between the electrodes. In this apparatus, beside the above problems (2) and (3) there is a third problem that the degree of membrane contact between adjacent cells is low and consequently the rate of fusion is low.

Accordingly, it is one object of the invention to provide an apparatus for fusing cells which can provide a substantially uniform field strength which is an important factor for cell fusion, so that it is possible to exactly know the effective strength of the electric field applied to the cells to be fused together, and wherein the cells do not stick to the electrodes but closely contact each other between the electrodes, so that it is possible to effect fusion of a single pair of cells without causing multi-fusion wherein many cells are fused together.

The cells to be fused are suspended in a solution, and the suspension is put in a space between a pair of opposed electrodes in a fusion chamber. If the amount of the suspension is relatively small such as, for example, 0.05 ml. small electrodes suffice and the chamber enclosing the electrodes can be of a simple shape and construction so that it is relatively easy to handle the chamber.

If the amount of the cell suspension, however, is relatively great such as, for example, 1 ml, the space between the electrodes and/or the length of the electrodes must be increased to accommodate the suspension. If the space between the electrodes is increased, the voltage applied to the electrodes must be increased, with resulting increase in the size of the instrument as a whole. If the length of the electrodes is increased, in order for a fusion chamber of a limited size to accommodate the elongated electrodes, the electrodes must be of a complicated shape. If long linear electrodes are used, the chamber must be elongated, with resulting decrease in the easiness of manipulation of the instrument.

Accordingly, it is another object of the invention to provide a fusion chamber which is small in size and simple in construction and yet capable of containing a sufficient amount of a suspension containing cells to be fused together.

Generally, when cells are fused by application of an electrical stimulus to them, it takes about 30 minutes for the fusion to be completed. During the process the ambient temperature and application of the electric field cause the temperature of the cell suspension to rise so that evaporation occurs to cause the osmotic pressure of the cell suspension to increase with resulting destruction of the cells.

Accordingly, it is still another object of the invention to provide a fusion chamber which can prevent excessive evaporation and decrease of the cell suspension.

SUMMARY OF THE INVENTION

Briefly stated, the apparatus of the invention comprises a fusion chamber in which fusion of cells is effected, a source of an alternating current (AC) and a direct current (DC) voltage, and a controller for effecting selective application of an AC field and a DC pulse to a cell suspension in the fusion chamber.

The fusion chamber includes a pair of electrodes having opposite surfaces spaced a distance apart from each other, with a cell suspension being put in the space between the electrodes. The opposite surfaces of the electrodes have such a vertical dimension or height in view of the size of the cells in the cell suspension as to prevent a substantial nonuniform electric field prevailing adjacent the upper edges of the electrodes from adversely affecting fusion of the cells. The floor of the fusion chamber between the electrodes is made of such a material or so finished as to provide a smooth flat surface.

In one embodiment of the invention, the electrodes comprises a pair of parallel plate electrodes spaced a distance apart from each other.

In another embodiment of the invention, the electrodes comprises a pair of hollow cylindrical electrodes having a relatively short axial length and concentrically arranged so that the outer one of the electrodes has an inner circumferential surface opposite the outer circumferential surface of the inner one of the electrodes. The radii of the two electrodes approximate each other so as to produce such a substantially uniform electric field as would be produced by parallel plate electrodes.

In a different embodiment of the invention, the fusion chamber has a cavity for containing a cell suspension and a separate cavity for containing a different liquid and is tightly closed by a lid or cover so as to prevent excessive evaporation of the liquid component of the cell suspension.

The invention will be described in detail with reference to the accompanying drawing.

DESCRIPTION OF PREFERRED EMBODIMENTS

Figure 1:
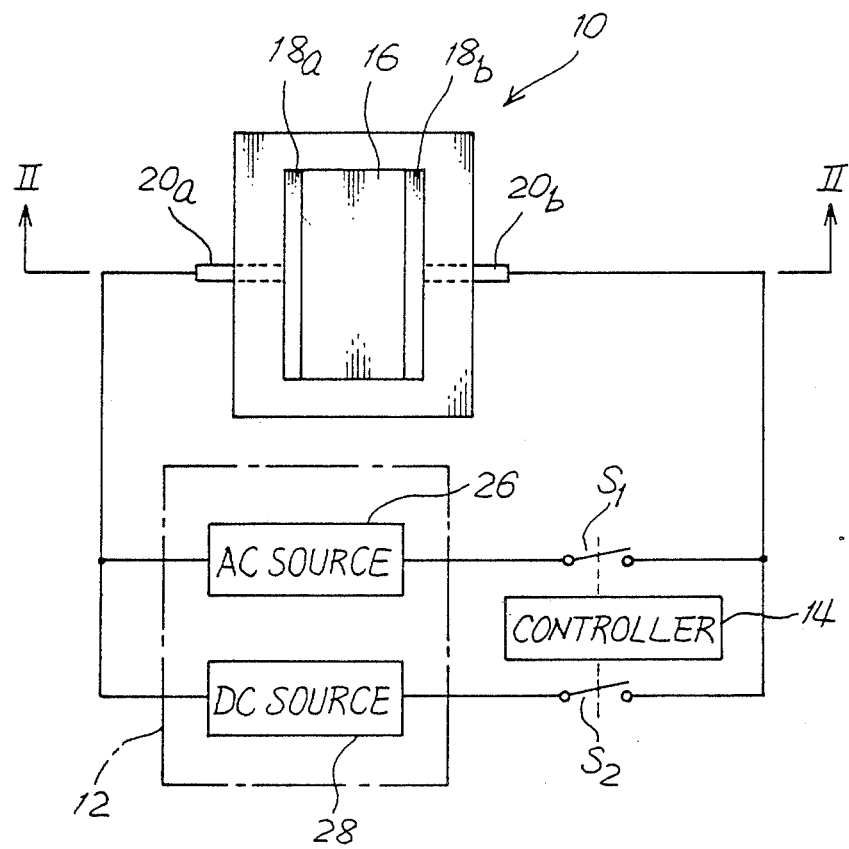
FIG. 1 is a schematic diagram of one embodiment of the invention.

It should be noted that in the drawing the relative dimensions of the component parts are not shown accurate but exaggerated for clarity of illustration, and that the dimensions of the parts should not be taken to limit the scope of the invention in any sense.

Figure 2:
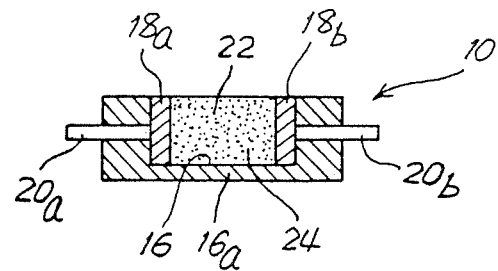
FIG. 2 is a vertical section taken along line II—II of the fusion chamber shown in FIG. 1.

Referring to FIGS. 1 and 2, there is shown an apparatus for fusing cells which comprises a fusion chamber 10, and a source 12 of electricity and a controller 14.

The fusion chamber 10 comprises a cavity 16 in which a pair of parallel plate electrodes 18a and 18b are provided and spaced apart from each other. The distance between the two electrodes 18a and 18b is determined in view of the source voltage so as to be as great as possible so long as an electric field strength necessary for effecting the intended cell fusion is obtained. The greater the height of the electrodes 18a and 18b is, the more cell suspension must be put between the electrodes. On the contrary, if the height of the electrodes is made too small, the nonuniform electric field caused adjacent the upper edges of the electrodes exerts an adverse influence on the cells. Therefore, the electrodes have such a height in view of the size of the cells as to prevent any nonuniform electric field from adversely affecting the process of cell fusion. The electrodes have a pair of terminals 20a and 20b for connection to the source 12.

The cavity 16 has a bottom wall 16a between the two electrodes 18a and 18b. The bottom wall 16a is made of a material which provides a flat and smooth upper surface.

A suspension 22 containing cells 24 to be fused together is put in the cavity 16 between the electrodes 18a and 18b.

The source 12 comprises an AC source 26 and a DC source 28, which are connected to the terminals 20a and 20b through switches $S_1$ and $S_2$, respectively, so that an AC and a DC voltage are alternatively applied to the electrodes 18a and 18b in the fusion chamber 10.

The cells 24 in the suspension 22 precipitate onto the bottom wall 16a of the cavity 16. By closing the switch $S_1$ an AC voltage having a predetermined frequency (within the range of 50 kHz to 5 MHz) is applied through the terminals 20a and 20b to the electrodes 18a and 18b thereby to generate an AC field therebetween, whereupon the cells 24 on the bottom wall surface 16a of the cavity 16 are lined in the direction of the electric field until adjacent cells are brought into close membrane contact with each other. Then the switch $S_1$ is opened and the switch $S_2$ is closed to apply a DC field to the cells to cause each adjacent pair of cells to be fused into a single cell.

Since the electrodes 18a and 18b are parallel plate electrodes, the strength of the AC electric field applied to the cells is substantially uniform between the electrodes. In addition, since the AC field causes the cells on the bottom wall surface of the cavity 16 in the fusion chamber 10 to be lined perpendicularly to the electrodes 18a and 18b, that is, in the same direction as that of the electric field, the field strength conforms substantially to the calculated value, so that it is possible to exactly know the strength of the electric field applied to the cells.

Since the bottom wall surface of the cavity 16 in the fusion chamber 10 is flat and smooth, the cells can move easily on the surface upon application of an AC field thereto.

In accordance with the invention, since an AC field is applied to the cells that have precipitated onto the bottom wall surface of the cavity 16, the electrodes 18a and 18b can have a smaller height than otherwise, and in order to contain as much cell suspension as possible, the electrodes are spaced apart from each other as great a distance as possible.

For a single pair of cells to be fused together the density or quantity of cells in the suspension must be adjusted preferably within a range of $10^4$/ml to $10^5$/ml.

With the apparatus of the invention, it is possible (1) to exactly know the effective electric field strength for cell fusion.

(2) to bring cells into close membrane contact with each other by application of an AC field to them, thereby to increase the efficiency of fusion.

(3) to cause cell fusion to be effected between the electrodes so that the fused cells can be taken out of the fusion chamber without any danger of damaging them, and (4) to obtain single pairs of fused cells.

Figure 3:
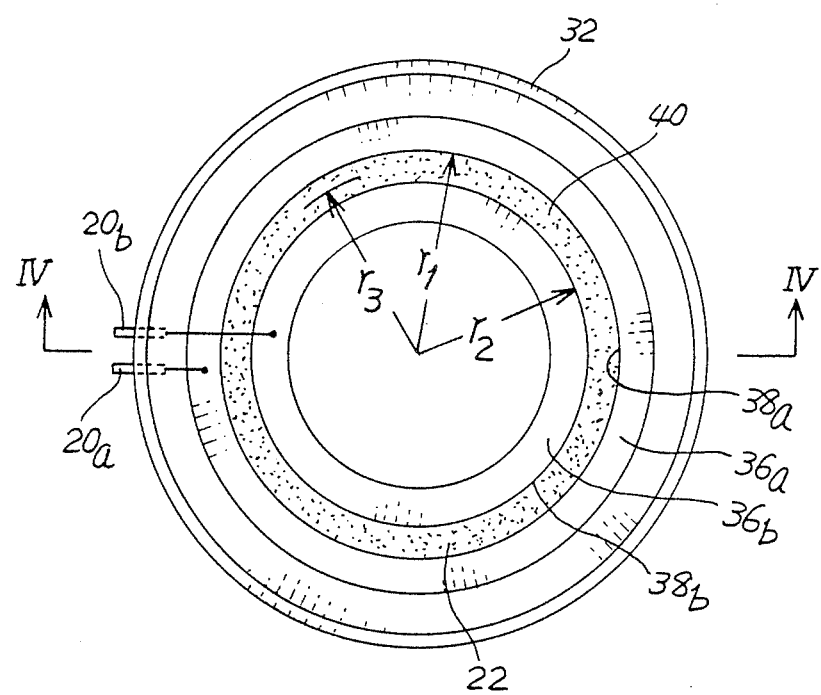
FIG. 3 is a somewhat schematic top plan view of another form of the fusion chamber, with the lid taken off.
Figure 4:
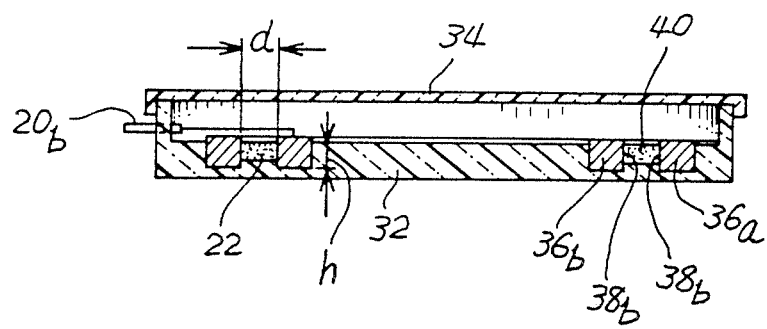
FIG. 4 is a vertical section taken along line IV—IV of the fusion chamber in FIG. 3, with the lid tightly closing the chamber.

Turning to FIGS. 3 and 4, wherein the same reference numerals as in FIGS. 1 and 2 designate corresponding component parts, there is shown a fusion chamber 10 comprising a shallow container 32 which is circular in transverse section and open upward, and a lid or cover 34 for airtightly closing the container.

A pair of hollow cylindrical electrodes 36a and 36b are concentrically arranged in a spaced apart relation to each other in the container and have an inner and an outer circumferential surface 38a and 38b, respectively, so as to define an annular space 40 therebetween. The electrodes 36a and 36b have a pair of terminals 20a and 20b which appear outside the container 32. As in the embodiment of FIGS. 1 and 2, the electrodes have such a height or axial length in view of the cells to be fused as to prevent any nonuniform electric field from exerting an adverse influence on formation of pairs of cells.

A cell suspension 22 is put in the annular space 40, and the lid or cover 34 tightly closes the container 32. First, an AC field is generated between the electrodes 36a and 36b to form pairs of cells in each of which two cells closely contact each other, and then a DC pulse is applied to the cells to cause fusion of each pair of cells.

The maximum quantity of the cell suspension 22 that fills the annular space 40 between the electrodes 36a and 36b is given as $1 \times d \times h$, that is, the product of the length $l$ ($= 2\pi r_3$) of the annular space 40, the distance (d) between the electrodes and the depth (h) of the space.

The field strength E(V/cm) of a pair of parallel electrodes is given as $E = V_o/d$ where $V_o$ is the voltage impressed across the two electrodes, and d is the distance between the two electrodes. The field strength E is uniform.

In the hollow cylindrical electrodes 36a and 36b, the field strengths $E_1$ and $E_2$ adjacent to the outer electrode 36a and the inner electrode 36b are given respectively as follows:

$$E_1 = K/r_1,$$

and $$E_2 = K/r_2$$

where K is a constant, $r_1$ is the radius of the inner circumference of the outer electrode 36a and $r_2$ is the radius of the outer circumference 38b of the inner electrode 36b.

Therefore, $E_1/E_2 = r_2/r_1$. If $r_1 \approx r_2$, $E_1 \approx E_2$, so that the strength of the electric field produced between the two electrodes 36a and 36b becomes approximately the same as that of the electric field produced between two parallel electrodes. The difference between the radii $r_1$ and $r_2$ is very small as compared with the radii. For example, $r_1$ is 50 mm and $r_2$ is 52 mm, so that the difference, that is, the above-mentioned distance d is 2 mm.

Since the hollow cylindrical electrodes 36a and 36b of the invention have their respective radii approximating each other, they have the following advantages:

(1) They have substantially the same electrical characteristics as parallel electrodes and enables cell fusion with substantially the same efficiency of fusion.

(2) The annular shape of the electrodes and concentric arrangement thereof enable simplification of the structure of the fusion chamber, particularly, that of the electrodes.

(3) The chamber can be made compact in size, so that it can be handled with ease on a microscope or in a clean bench.

Figure 5:
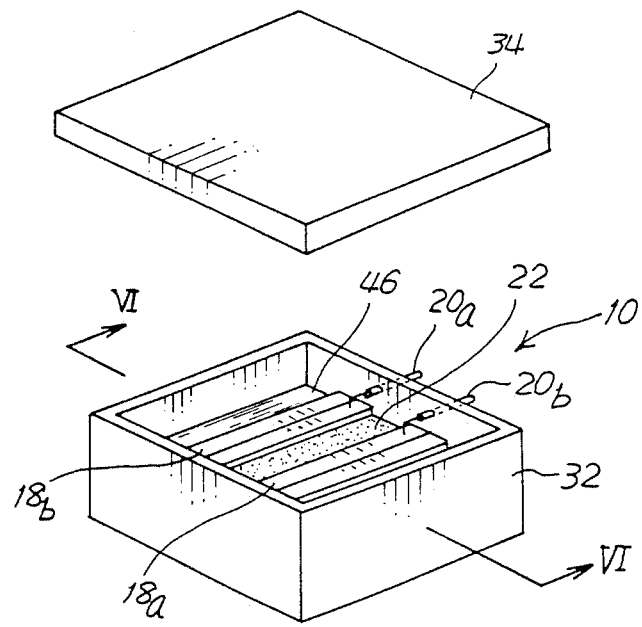
FIG. 5 is a somewhat schematic perspective view of a third form of the fusion chamber.
Figure 6:
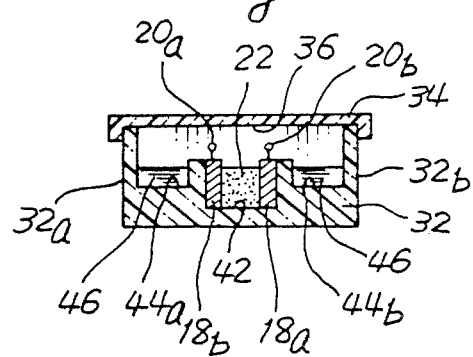
FIG. 6 is a vertical section taken along line VI—VI of the fusion chamber shown in FIG. 5.

Now turning to FIGS. 5 and 6, there is shown a fusion chamber 10 comprising a container 32 open upward and a lid or cover 34 for airtightly closing the container 32. Both the container 32 and the lid 34 are square in transverse section. The container 32 is formed in the inner bottom surface thereof with a central groove or cavity 42 and a pair of side grooves or cavities 44a and 44b at the outer opposite sides of the central cavity 42.

A pair of spaced parallel plate electrodes 18a and 18b are provided in the central cavity 42. As in the previous embodiments, the electrodes are of such a height as to prevent any nonuniform electric field from adversely affecting formation of pairs of cells.

A cell suspension 22 is put in the central cavity 42 while a liquid 46 such as for example water is put in the side cavities 44a and 44b.

When the lid 34 is placed on the container 32, the downwardly facing inner surface 36 of the lid 34 closely contacts the upper edge surfaces of the side walls 32a and 32b of the container 32 thereby to airtightly enclose the cell suspension 22 in the cavity 42 and the water in the cavities 44a and 44b within the same space in the fusion chamber 10.

Under the condition, an AC voltage is applied to the electrodes 18a and 18b through the terminals 20a and 20b to generate an AC field therebetween thereby to form pairs of cells, whereupon a DC pulse is applied to the pairs of cells to fuse each pair into a single cell.

During the process the temperature of the cell suspension 22 is raised due to the ambient temperature and the application of an AC field thereto so that the liquid component of the suspension 22 begins to evaporate. However, the lid 34 prevents the vapor from emerging out of the chamber 10, so that the vapor pressure rises to prevent further evaporation of the suspension 22. At the same time, evaporation of the water 46 in the side cavities 44a and 44b helps prevent evaporation of the suspension 22.

Since evaporation of the cell suspension 22 is suppressed to the minimum, it is possible for a process of cell fusion to continue for a longer time than otherwise without adversely affecting the cells in the suspension.

Figure 4A:
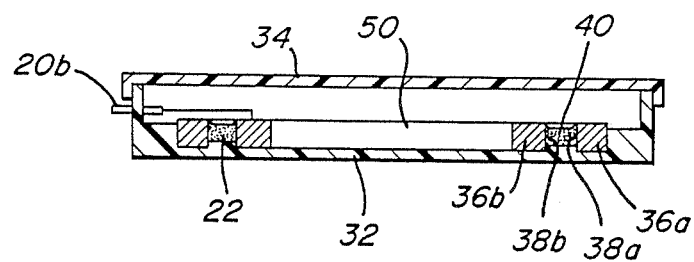
FIG. 4a is a modification of the embodiment of FIGS. 3 and 4.

It is possible to employ a cavity for holding water in any of the previous embodiments. For example, FIG. 4a shows the fusion chamber of FIGS. 3 and 4 with a central cavity 50 defined by the inner circumference of the inner electrode 36b. Like the embodiment of FIGS. 5 and 6, the water in the cavity 50 helps prevent evaporation of the suspension 22.

Figure 7:
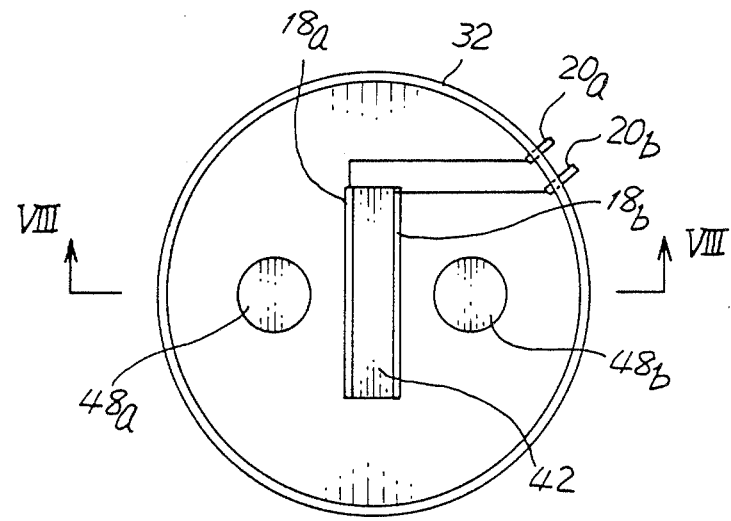
FIG. 7 is a somewhat schematic top plan view of a modified form of the fusion chamber shown in FIGS. 5 and 6.
Figure 8:
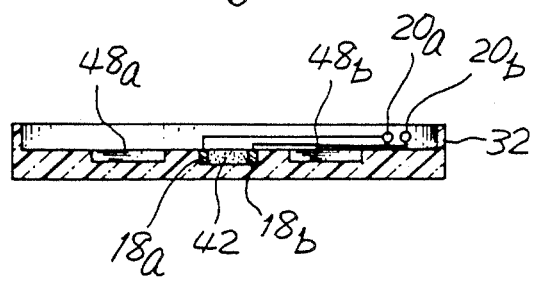
FIG. 8 is a vertical section taken along line VIII—VIII of the fusion chamber shown in FIG. 7.

FIGS. 7 and 8 show a modified form of the fusion chamber shown in FIGS. 5 and 6. The same reference numerals as in FIGS. 5 and 6 designate corresponding parts. The container 32 is circular and formed with a central rectangular cavity 42 and a pair of circular pits 48a and 48b at the opposite sides of the cavity 42. A pair of parallel plate electrodes 18a and 18b are provided in the cavity 42, with a pair of terminals 20a and 20b for connection to an AC and a DC voltage source, not shown.

In any of the above-mentioned embodiments of the invention, the bottom wall of the fusion chamber may be made of a transparent material at least between the electrodes so that the process of cell fusion with an electric field being applied to the cells can be observed through the transparent bottom wall with an inverted microscope. In this case the lid must be of such a material as to pass light for illumination.

What we claim is:

1. An apparatus for fusing cells comprising:
   a fusion chamber including a pair of electrodes having opposite surfaces spaced a predetermined distance apart from each other to define a space therebetween in which a cell suspension is locateable, said opposite surfaces having a height which is sufficient, in view of sizes of cells in said cell suspension, to prevent any possible nonuniform electric field adjacent edges of said electrodes from adversely affecting a process of cell fusion;
   means for producing an alternating current voltage;
   means for producing a direct current voltage;
   means for effecting selective application of said AC and DC voltage to said electrodes;
   a removable lid for airtightly closing said fusion chamber; and
   a cavity for containing said pair of electrodes and said cell suspension therebetween, and at least one additional cavity for containing a different fluid.

2. The apparatus of claim 1, wherein said electrodes are a pair of parallel plate electrodes.

3. The apparatus of claim 1, wherein said electrodes comprise an outer cylindrical electrode having an inner circumferential surface of a first radius and an inner cylindrical electrode having an outer circumferential surface of a second radius smaller than said first radius and bieng concentrically disposed in said outer electrode, a difference in length between said first and second radii being sufficiently small, compared with a length of either of said radii, as to provide for a substantially uniform electric field as generally produceable by parallel plate electrodes.

4. The apparatus of claim 1, and further comprising a floor of said fusion chamber having a flat and smooth surface between said electrodes.

5. The apparatus of claim 1, and further comprising a floor of said fusion chamber being transparent at least between said electrodes.

6. The apparatus of claim 1, and further comprising a removable lid for airtightly closing said fusion chamber.

7. The apparatus of claim 1, wherein said pair of electrodes are of a circular shape of different radii and concentrically arranged in said first cavity, wherein said additional cavity is defined by an inner wall of the electrode having a smaller radius.

8. A fusion chamber for use in an apparatus for fusing cells, comprising:
 a container provided in a bottom wall thereof with a cavity for containing a cell suspension;
 a pair of electrodes disposed in said cavity and having electrode surface each having a height which is sufficient, in view of sizes of cells in said cell suspension, to prevent any possible nonuniform electric field from adversely affecting a process of cell fusion;
 a removable lid for airtightly closing said fusion chamber; and
 at least one additional cavity located in the bottom wall of said container for containing a different liquid.

9. The fusion chamber of claim 8, wherein said electrodes comprise parallel plate electrodes.

10. The fusion chamber of claim 8, wherein said electrodes comprise an outer cylindrical electrode having an inner circumferential surface of a first radius and an inner cylindrical electrode having an outer circumferential surface of a second radius smaller than said first radius and being concentrically disposed in said outer electrode, a difference in length between said first and second radii being sufficiently small, compared with a length of either of said radii, as to provide for a substantially uniform electric field as generally produceable by parallel plate electrodes.

11. The fusion chamber of claim 8, having a floor of said fusion chamber with a flat and smooth surface between said electrodes.

12. The fusion chamber of claim 8, having a floor of said fusion chamber transparent at least between said electrodes.

13. The fusion chamber of claim 12, wherein said lid is made of a material which passes light for illumination.

* * * * *